(12) United States Patent
Satake

(10) Patent No.: US 12,042,131 B2
(45) Date of Patent: Jul. 23, 2024

(54) ENDOSCOPE DISTAL END PORTION HAVING CONDUCTIVE ELASTICALLY DEFORMABLE MEMBER AND ENDOSCOPE HAVING THE DISTAL END PORTION

(71) Applicant: OLYMPUS CORPORATION, Tokyo (JP)

(72) Inventor: Nau Satake, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 475 days.

(21) Appl. No.: 17/372,689

(22) Filed: Jul. 12, 2021

(65) Prior Publication Data

US 2021/0338057 A1 Nov. 4, 2021

Related U.S. Application Data

(63) Continuation of application No. PCT/JP2019/001087, filed on Jan. 16, 2019.

(51) Int. Cl.
*A61B 1/05* (2006.01)
*A61B 1/00* (2006.01)
*A61B 1/018* (2006.01)

(52) U.S. Cl.
CPC ............ *A61B 1/05* (2013.01); *A61B 1/00087* (2013.01); *A61B 1/00096* (2013.01); *A61B 1/00148* (2022.02); *A61B 1/018* (2013.01)

(58) Field of Classification Search
CPC ... A61B 1/05; A61B 1/00087; A61B 1/00096; A61B 1/00148; A61B 1/018; A61B 2562/182
See application file for complete search history.

(56) References Cited

U.S. PATENT DOCUMENTS 4,960,106 A * 10/1990 Kubokawa ............ A61B 1/0055
  600/116
11,304,599 B2 * 4/2022 Komoro ................. G02B 23/24
(Continued)

FOREIGN PATENT DOCUMENTS

JP    2009-101077 A    5/2009
JP    2015-039410 A    3/2015
(Continued)

OTHER PUBLICATIONS

International Search Report dated Mar. 12, 2019 issued in PCT/JP2019/001087.

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

An endoscope distal end portion includes: an imaging unit including an imaging element configured to capture a subject image, and a reinforcement frame made of metal, the reinforcement frame being configured to hold the imaging element; a distal end frame including an insulating member and having a through-hole through which the imaging unit is inserted; a conductive exterior member having a distal end side connected to a proximal end side of the distal end frame and a proximal end side connected to a ground of an external device; and a conductive member including an electroconductive member, one end thereof being electrically and mechanically connected to the reinforcement frame, a part thereof being electrically connected to the exterior member.

4 Claims, 7 Drawing Sheets

(56) References Cited

U.S. PATENT DOCUMENTS

| | | | |
|---|---|---|---|
| 11,659,981 B2* | 5/2023 | Hatase | A61B 1/01 600/109 |
| 2009/0112060 A1 | 4/2009 | Postolov et al. | |
| 2012/0271108 A1 | 10/2012 | Hoshino | |
| 2013/0015873 A1* | 1/2013 | Suzuki | H01R 13/6471 324/755.02 |
| 2013/0310644 A1* | 11/2013 | Ichimura | A61B 1/051 600/109 |
| 2020/0015664 A1* | 1/2020 | Hatase | A61B 1/07 |
| 2020/0120782 A1* | 4/2020 | Nakao | A61B 1/00071 |
| 2021/0275005 A1* | 9/2021 | Yoshida | G02B 23/2484 |
| 2021/0338057 A1* | 11/2021 | Satake | A61B 1/00087 |

FOREIGN PATENT DOCUMENTS

| | | |
|---|---|---|
| JP | 2017-209278 A | 11/2017 |
| WO | 2011/089777 A1 | 7/2011 |

* cited by examiner

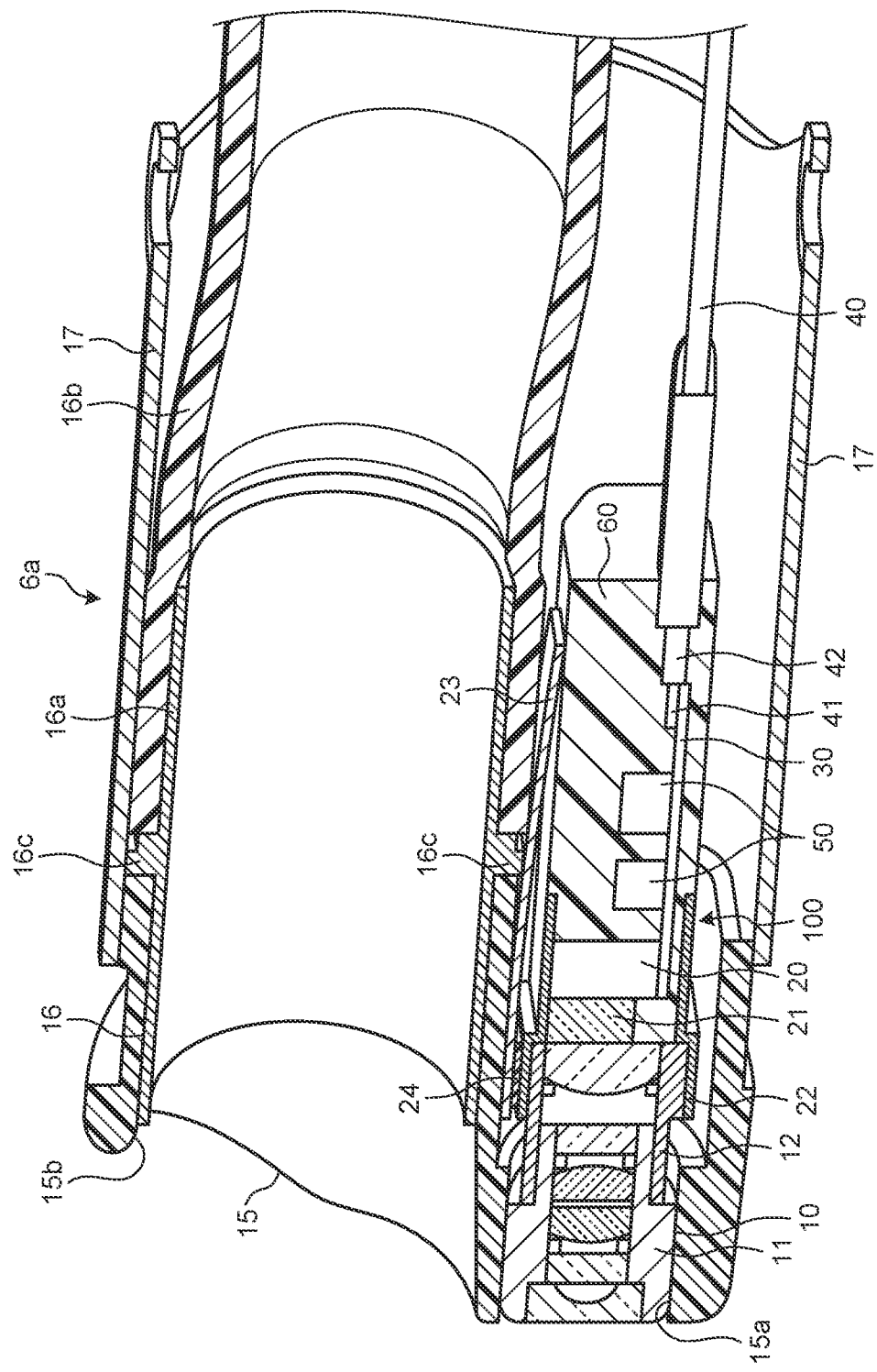

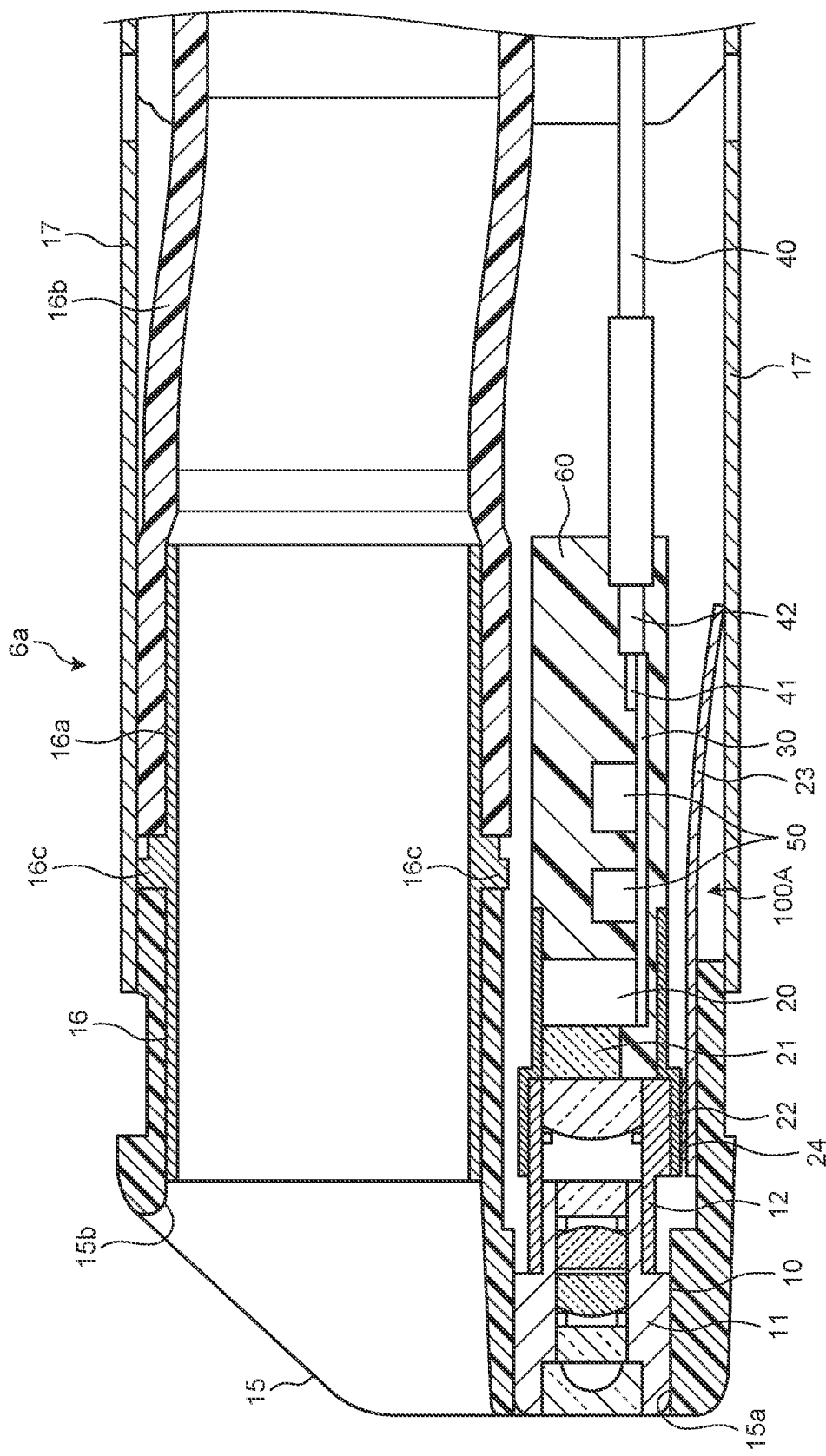

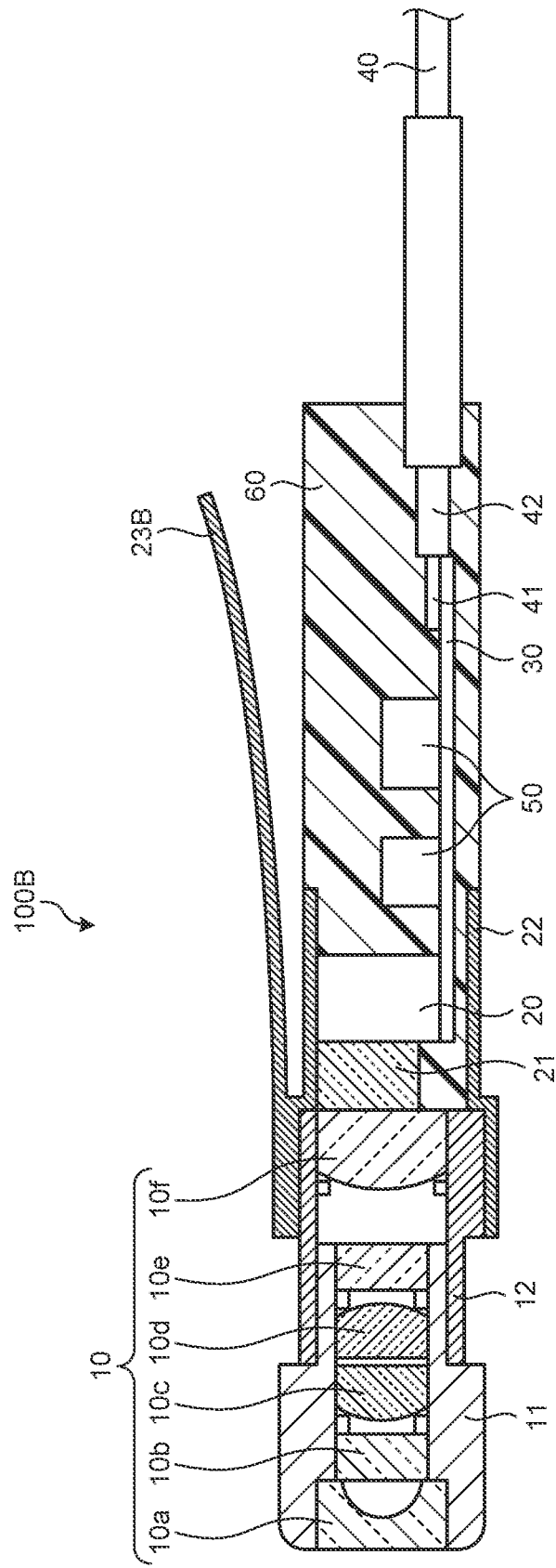

ENDOSCOPE DISTAL END PORTION HAVING CONDUCTIVE ELASTICALLY DEFORMABLE MEMBER AND ENDOSCOPE HAVING THE DISTAL END PORTION

This application is a continuation of International Application No. PCT/JP2019/001087, filed on Jan. 16, 2019, the entire contents of which are incorporated herein by reference.

BACKGROUND

The present disclosure relates to an endoscope distal end portion and an endoscope.

In the related art, an endoscope acquires image data in a subject by means of an imaging unit arranged at a distal end portion thereof by inserting a flexible insertion unit having an elongated shape provided with an imaging unit at the distal end into the subject, and transmits the image data to an external information processing device by means of a signal cable.

Although an endoscope has been proposed recently in which a distal end frame of the insertion unit is switched from a metal to a resin, in order to use a member made of resin, a mechanism for preventing an imaging element from being damaged when static electricity is applied is required.

As a technique for preventing leakage current and static electricity from flowing into an imaging element, an endoscope has been proposed in which a circuit pattern is provided on the inner peripheral face of a fixing hole to which a lens frame of the distal end frame is fixed, and the circuit pattern is connected to a bending tube which is a conductive member.

SUMMARY

According to one aspect of the present disclosure, there is provided an endoscope distal end portion including: an imaging unit including an imaging element configured to capture a subject image, and a reinforcement frame made of metal, the reinforcement frame being configured to hold the imaging element; a distal end frame including an insulating member and having a through-hole through which the imaging unit is inserted; a conductive exterior member having a distal end side connected to a proximal end side of the distal end frame and a proximal end side connected to a ground of an external device; and a conductive member including an electroconductive member, one end thereof being electrically and mechanically connected to the reinforcement frame, a part thereof being electrically connected to the exterior member.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 5 is a perspective view of a cross section of the distal end portion of FIG. 4;

FIG. 6 is a cross-sectional view of a distal end portion according to a modification of the first embodiment; and FIG. 7 is a cross-sectional view of an imaging unit according to a second embodiment.

DETAILED DESCRIPTION

Figure 1:
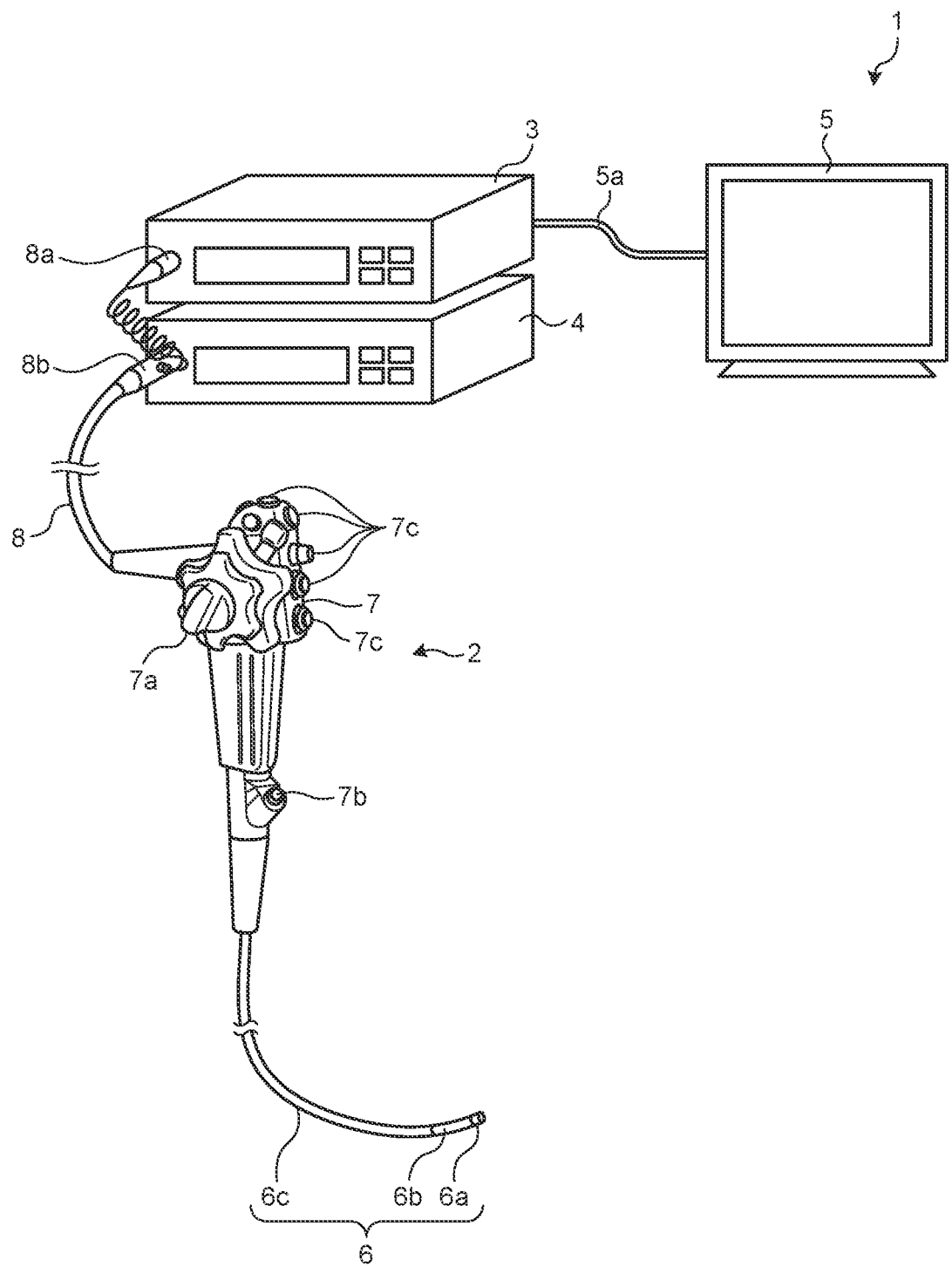
FIG. 1 is a view schematically illustrating an overall configuration of an endoscope system according to a first embodiment.

In the following description, an endoscope system including an endoscope distal end portion will be described as a mode for carrying out the present disclosure (hereinafter referred to as "embodiment"). The present disclosure is not limited by this embodiment. Further, in the drawings, the same portions are denoted by the same reference numerals. Further, it is necessary to note that the drawings are schematic illustration in which the relationships between the thickness and the width of each member, and the proportions of each member, for example, may differ from the actual relationships and proportions. In addition, there may be differences in dimensions and proportions between the drawings.

FIG. 1 is a view schematically illustrating an overall configuration of an endoscope system 1 according to a first embodiment. As illustrated in FIG. 1, the endoscope system 1 according to the first embodiment includes: an endoscope 2 which is introduced into a subject and captures the inside of the subject to generate an image signal of the inside of the subject; an information processing device 3 which performs predetermined image processing on the image signal obtained by the capturing by the endoscope 2 and controls each part of the endoscope system 1; a light source device 4 which generates illumination light of the endoscope 2; and a display device 5 which displays the image signal after image processing by the information processing device 3.

The endoscope 2 includes an insertion unit 6 inserted into the subject, an operating unit 7 held by an operator on the proximal end portion side of the insertion unit 6, and a flexible universal cord 8 extending from the operating unit 7.

The insertion unit 6 is implemented by using a light guide cable, an electric cable, and an optical fiber, for example. The insertion unit 6 has a distal end portion 6a which incorporates an imaging unit to be described below, a bendable bending portion 6b including a plurality of bending pieces, and a flexible tube portion 6c provided on the proximal end portion side of the bending portion 6b. The distal end portion 6a is provided with a light guide cable for illuminating the inside of the subject, an imaging unit for capturing the inside of the subject, and an opening for communicating a channel for a treatment tool.

The operating unit 7 has: a bending knob 7a for bending the bending portion 6b in the vertical and horizontal directions; a treatment tool insertion portion 7b in which treatment tools such as biological forceps and a laser scalpel are inserted into the body cavity of the subject; and a plurality of switch portions 7c for operating peripheral devices such as the information processing device 3, the light source device 4, an air supply device, a water supply device, and a gas supply device. The treatment tool inserted from the treatment tool insertion portion 7b comes out from the opening of the distal end of the insertion unit 6 through a treatment tool channel provided inside of the insertion unit.

The universal cord 8 is formed by using a light guide cable, and an electric cable, for example. The universal cord 8 is branched at its proximal end. One of the branched ends is a connector 8a and the other proximal end is a connector 8b. The connector 8a is attachable to and detachable from a connector of the information processing device 3. The connector 8b is attachable to and detachable from the light source device 4. The universal cord 8 propagates the illumination light emitted from the light source device 4 to the distal end portion 6a via the connector 8b and the light guide cable. Further, the universal code 8 transmits the image signal obtained by capturing by the imaging unit to be described below to the information processing device 3 via the cable and the connector 8a.

The information processing device 3 performs predetermined image processing on the image signal outputted from the connector 8a and controls the entire endoscope system 1.

The light source device 4 is formed by using a light source for emitting light, and a condenser lens, for example. Under the control of the information processing device 3, the light source device 4 emits light from the light source and supplies the light to the endoscope 2 connected via the light guide cable of the connector 8b and the universal cord 8 as illumination light for the inside of the subject which is a subject to be imaged.

The display device 5 is formed by using, for example, a display using a liquid crystal or an organic EL (Electro Luminescence). The display device 5 displays various types of information including the images having been subjected to the predetermined image processing by the information processing device 3 via a video cable 5a. Thus, the surgeon may observe and determine properties of a desired position of the inside of the subject by operating the endoscope 2 while viewing the image (in-vivo image) displayed on the display device 5.

Figure 2:
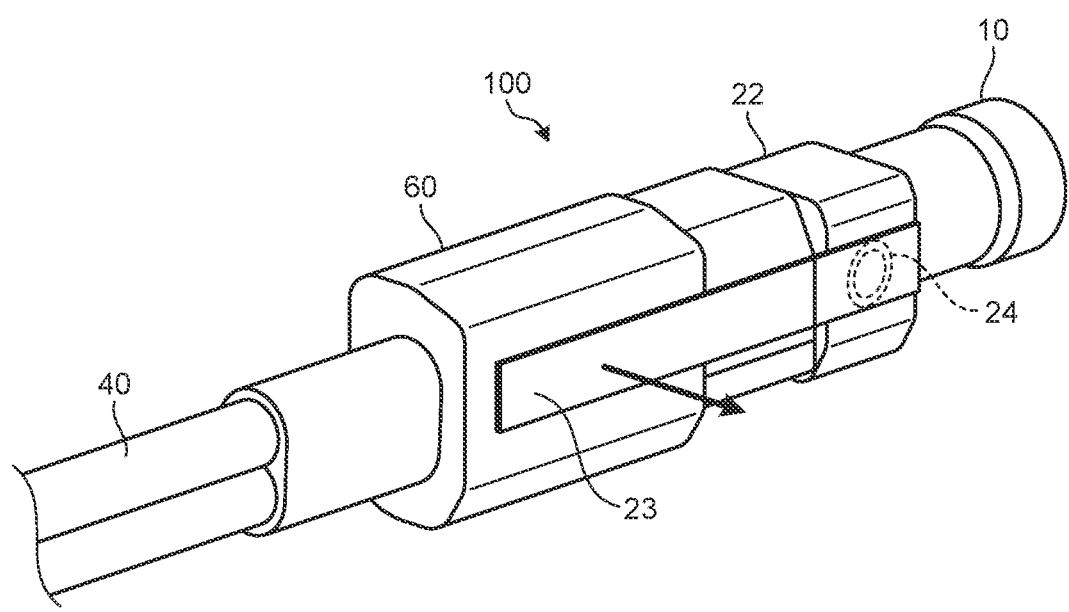
FIG. 2 is a perspective view of an imaging unit used in the endoscope illustrated in FIG. 1.
Figure 3:
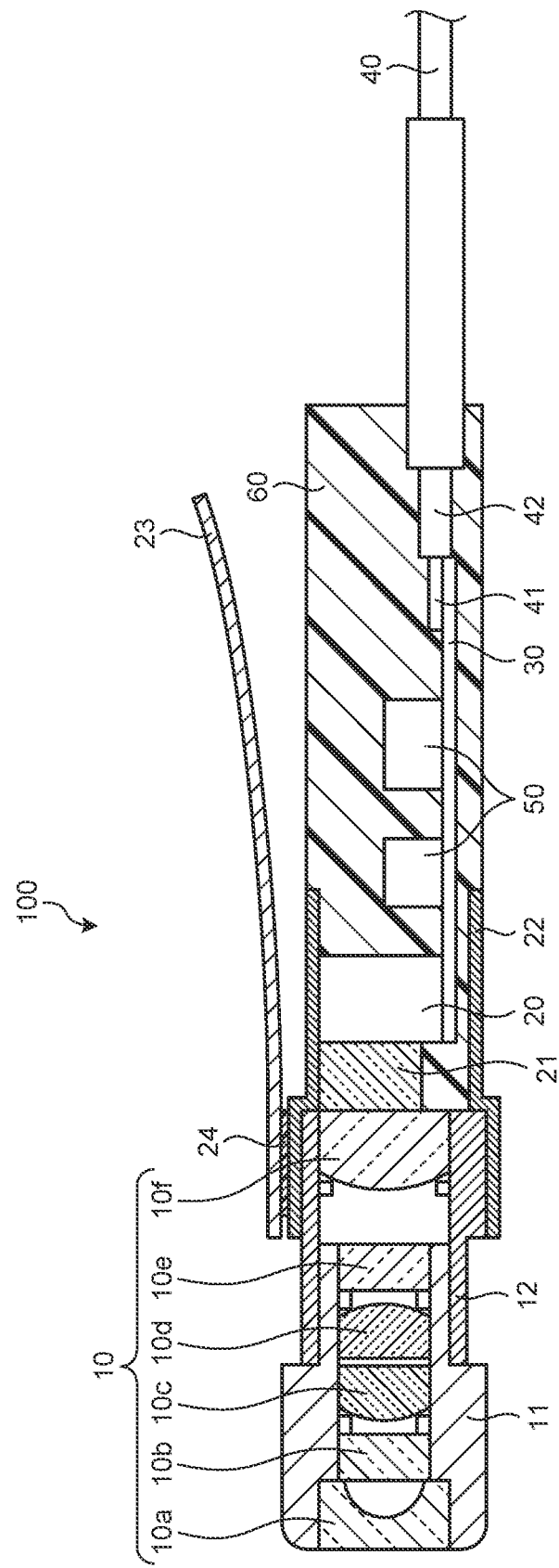
FIG. 3 is a cross-sectional view of the imaging unit illustrated in FIG. 2.
Figure 4:
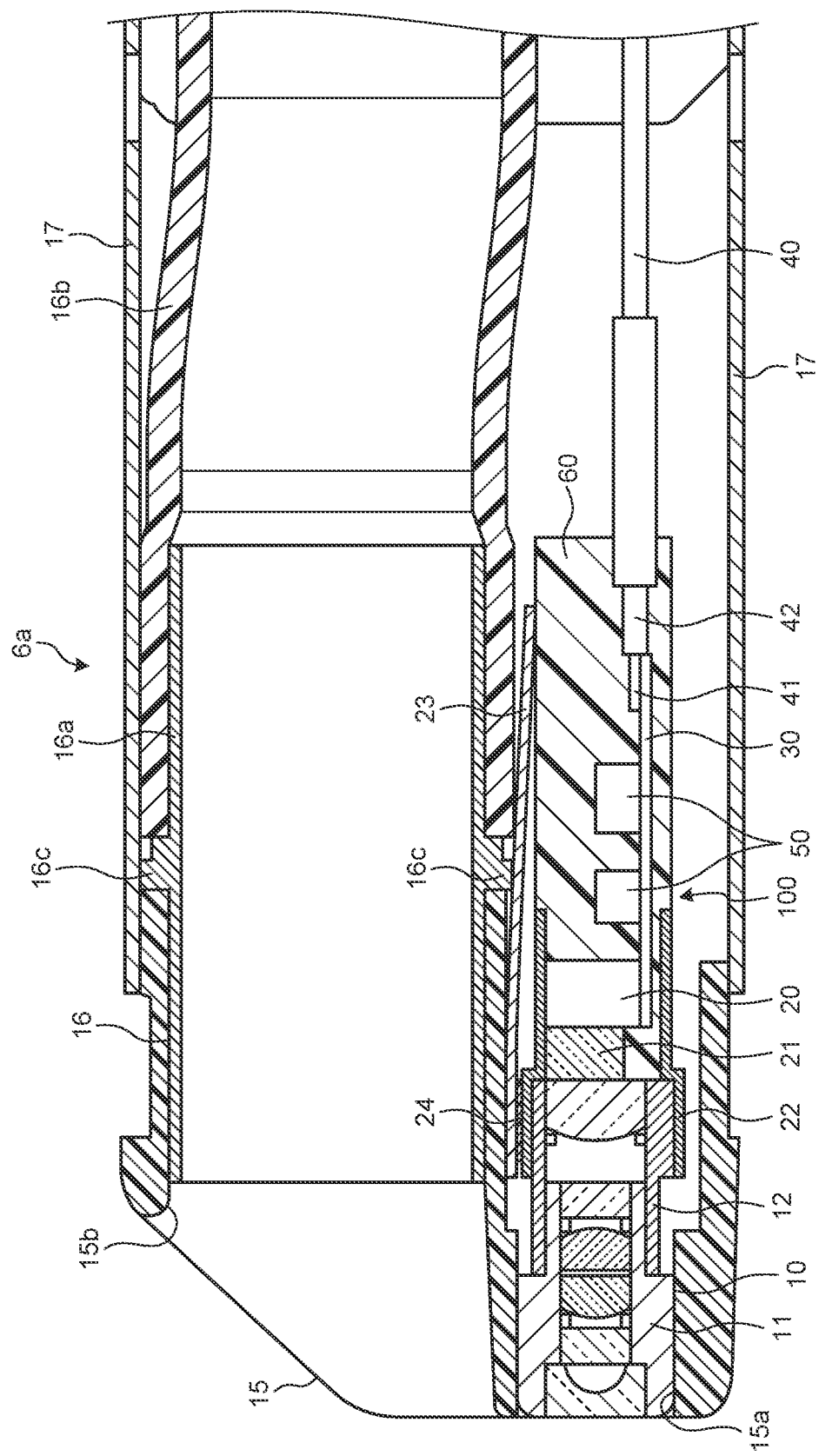
FIG. 4 is a cross-sectional view of a distal end portion of the endoscope illustrated in FIG. 1.

The distal end portion 6a used in the endoscope system 1 will then be described in detail. FIG. 2 is a perspective view of an imaging unit 100 used in the endoscope 2 illustrated in FIG. 1. FIG. 3 is a cross-sectional view of the imaging unit 100 illustrated in FIG. 2. FIG. 4 is a cross-sectional view of the distal end portion 6a of the endoscope 2 illustrated in FIG. 1. FIG. 5 is a perspective view of a cross section of the distal end portion 6a of FIG. 4. FIGS. 4 and 5 omit illustration of external coatings. In the present description, the distal end portion 6a side of the endoscope 2 is referred to as a distal end side, and the side on which a signal cable 40 extends is referred to as a proximal end side.

The distal end portion 6a of the endoscope 2 includes: an imaging unit 100 for capturing a subject image; a treatment tool channel 16 through which the treatment tool is inserted; a distal end frame 15 having a through-hole 15a through which the imaging unit 100 is inserted and a channel through-hole 15b through which the treatment tool channel 16 is inserted; and a bending tube 17 for bending the distal end portion 6a vertically, or horizontally and vertically.

The imaging unit 100 includes: an optical unit 10 for forming an image of the subject; an imaging element 20 for photoelectrically converting the subject image formed by the optical unit 10 to generate an image signal; a circuit board 30; and a signal cable 40.

The optical unit 10 has a first lens 10a, a second lens 10b, a third lens 10c, a fourth lens 10d, a fifth lens 10e, and a sixth lens 10f in this order from the distal end side to the proximal end side along the optical axis.

The first lens 10a, the second lens 10b, the third lens 10c, the fourth lens 10d and the fifth lens 10e are held in a cylindrical first lens frame 11 made of metal. The first lens frame 11 is fixed to the distal end side of the through-hole 15a of the distal end frame 15 with an adhesive.

The sixth lens 10f is held in a cylindrical second lens frame 12 made of metal. The distal end side of the second lens frame is externally fitted to the proximal end side of the first lens frame 11 and fixed with a conductive adhesive.

A glass cover 21 for protecting a light receiving portion is bonded and fixed to the imaging element 20, and the face of the glass cover 21 on the opposite side of the bonding face to the imaging element 20 is fixed to the sixth lens 10f with an adhesive. The periphery of the imaging element 20 is covered with a reinforcement frame 22 made of metal, and the distal end side of the reinforcement frame 22 is externally fitted to the proximal end side of the second lens frame 12 and fixed with a conductive adhesive.

The imaging element 20 is mounted on the distal end side of the circuit board 30, and an electronic component 50 such as a transistor or a capacitor is mounted on the circuit board 30. Further, the circuit board 30 is connected to a signal cable 40 which transmits power and various signals to or image signals from the imaging element, on its proximal end side. The signal cable 40 is such that an insulating jacket 42 on the distal end side of the signal cable is removed to expose a core wire 41 and the exposed core wire 41 is connected to the circuit board 30 by a conductive material such as solder, which is not illustrated in the figure.

The inside of the reinforcement frame 22 (the periphery of the imaging element 20), the mounting region of the electronic component 50 of the circuit board 30 and the periphery of the connection region of the signal cable 40 are sealed with a sealing resin 60.

The reinforcement frame 22 has an end portion of a conductive member 23 including an electroconductive member electrically and mechanically fixed to its outer periphery with a conductive adhesive 24. The conductive member 23 may be, for example, a leaf spring made of metal. The conductive member 23 includes a member which is elastically deformed, and is urged in a direction to separate its other end side from the imaging unit 100. Instead of the adhesive 24, the conductive member 23 may be fixed to the reinforcement frame 22 with a conductive material such as solder.

The treatment tool channel 16 has a frame member 16a made of metal, a tube 16b made of resin externally fitted to the proximal end side of the frame member 16a, and a projection portion 16c provided around the outer face of the frame member 16a. The tube 16b is flexible and fixed to the frame member 16a with an adhesive.

Upon being inserted through the channel through-hole 15b of the distal end frame 15, the treatment tool channel 16 is aligned by abutting the projection portion 16c onto the distal end frame 15, and the frame member 16a of the treatment tool channel 16 is fixed to the channel through-hole 15b of the distal end frame 15 with an adhesive.

The distal end portion of the bending tube 17 is attached to a part of the face on the proximal end side of the projection portion 16c and the proximal end portion of the distal end frame 15. The bending tube 17 is a bending piece set in which a plurality of bending pieces including conductive members are rotatably connected by rivets. The bending piece is rotated around the rivet by pulling and loosening a wire arranged vertically and horizontally by the operation of the bending knob 7a, and the bending portion 6b is operated vertically or horizontally. In the present embodiment, the bending tube 17 functions as a conductive exterior member. An insulating sheath tube, which is not illustrated in the figure, is provided around the bending tube 17.

As illustrated in FIGS. 4 and 5, the imaging unit 100 is inserted through the through-hole 15a for the purpose of positioning the conductive member 23 in the direction of the treatment tool channel 16, and a part of the conductive member 23 abuts onto the projection portion 16c formed on the frame member 16a.

In the case where the distal end frame 15 made of a resin having no conductivity is employed in the distal end portion 6a of the endoscope 2, when static electricity or leakage current is applied, electrical conduction to the ground of the operating unit 7, for example, cannot be performed by the conductive member, which thereby may damage the imaging element 20. In the first embodiment, when static electricity, for example, is applied to the distal end portion 6a, electrical conduction from the conductive first lens frame 11, the second lens frame 12, the reinforcement frame 22, and the conductive member 23 via the frame member 16a of the treatment tool channel 16 and the bending tube 17 to the ground of the operating unit 7, for example, may be performed, which thereby may prevent the imaging element 20 from being damaged.

Further, in the first embodiment, the conductive member 23 includes a member that is elastically deformed, and is urged in a direction to separate its other end side from the imaging unit 100, so that the conductive member may securely abut onto the projection portion 16c.

Although the above-described first embodiment is such that a part of the conductive member 23 is arranged so as to abut onto the projection portion 16c formed on the frame member 16a, the first embodiment is not limited thereto. FIG. 6 is a cross-sectional view of a distal end portion 6a according to a modification of the first embodiment.

An imaging unit 100A according to the modification is inserted through the through-hole 15a for the purpose of positioning the conductive member 23 in the direction opposite to the treatment tool channel 16, that is, in the direction of the adjacent bending tube 17, and the other end of the conductive member 23 abuts onto the bending tube 17.

In the modification, when static electricity, for example, is applied to the distal end portion 6a, electrical conduction from the conductive first lens frame 11, the second lens frame 12, the reinforcement frame 22, and the conductive member 23 directly via the bending tube 17 to the ground of the operating unit 7, for example, may be performed, which thereby may prevent the imaging element 20 from being damaged.

In the first embodiment, the conductive member 23 is urged in a direction to separate its the other end side from the imaging unit 100, but the conductive member is not limited thereto. The conductive member may be, for example, a convex shape urged for the purpose of which its end portion is connected to the reinforcement frame 22, its central portion is urged in a direction to separate from the imaging unit 100, and the other end side is approached to the imaging unit 100.

Further, the sealing resin 60 may be formed using a material having elasticity, a protruding portion made of the sealing resin 60 may be provided at a position adjacent to the frame member 16a, and the conductive member 23 may be brought into contact with the frame member 16a by the elastic force of the protruding portion.

Alternatively, a conductive member may be formed by applying an adhesive having conductivity and elasticity from the reinforcement frame 22 to a position adjacent to the frame member 16a of the sealing resin 60.

In the second embodiment, the conductive member is integrally formed with the reinforcement frame. FIG. 7 is a cross-sectional view of an imaging unit 100B according to the second embodiment.

In the imaging unit 100B according to the second embodiment, the conductive member 23B is integrally formed with the reinforcement frame 22 without using an adhesive.

In the second embodiment, when static electricity, for example, is applied to the distal end portion 6a, electrical conduction from the conductive first lens frame 11, the second lens frame 12, the reinforcement frame 22, and the conductive member 23B via the frame member 16a of the treatment tool channel 16 and the bending tube 17 to the ground of the operating unit 7, for example, may be performed, which thereby may prevent the imaging element 20 from being damaged.

Alternatively, the conductive member 23B may be formed in a direction opposite to the treatment tool channel 16 of the reinforcement frame 22, that is, in the direction of the adjacent bending tube 17 and directly abut onto the bending tube 17. Thus, when static electricity, for example, is applied to the distal end portion 6a, electrical conduction from the conductive first lens frame 11, the second lens frame 12, the reinforcement frame 22, and the conductive member 23B directly via the bending tube 17 to the ground of the operating unit 7, for example, may be performed, which thereby may prevent the imaging element 20 from being damaged.

The distal end portion of the endoscope is useful for an endoscope system that requires a reduced diameter and a lower cost.

The present disclosure may obtain an endoscope distal end portion including a member made of resin which may prevent the imaging unit from being damaged by, for example, static electricity.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general concept as defined by the appended claims and their equivalents.

What is claimed is:

1. An endoscope distal end portion comprising:
   an imaging unit including
     an image sensor configured to capture a subject image, and
     a reinforcement frame made of metal, the reinforcement frame being configured to hold the image sensor;
   a distal end frame including an insulating member and having a through-hole through which the imaging unit is inserted;
   a conductive exterior member having a distal end side connected to a proximal end side of the distal end frame and a proximal end side connected to a ground of an external device; and
   a conductive member including an electroconductive member, one end thereof being electrically and mechanically connected to the reinforcement frame, a part thereof being electrically connected to the exterior member;
   wherein the conductive member is configured to elastically deform and is urged in a direction to separate the conductive member from the imaging unit.

2. The endoscope distal end portion according to claim 1, further comprising a frame member made of metal,
a tube made of resin externally fitted to a proximal end side of the frame member, and
a projection portion provided around an outer face of the frame member, wherein
the distal end frame includes a channel through-hole through which at least a portion of the frame member is inserted,
the frame member is positioned by abutting the projection portion onto the distal end frame, and connected by abutting the exterior member onto a face on a proximal end side of the projection portion, and
the conductive member is electrically connected to the exterior member by coming into contact with the projection portion.

3. The endoscope distal end portion according to claim 1, wherein the conductive member is integrally formed with the reinforcement frame.

4. An endoscope comprising
an endoscope distal end portion at an insertion unit thereof, the endoscope distal end portion including:
an imaging unit including
an image sensor configured to capture a subject image, and
a reinforcement frame made of metal, the reinforcement frame being configured to hold the image sensor;
a distal end frame including an insulating member and having a through-hole through which the imaging unit is inserted;
a conductive exterior member having a distal end side connected to a proximal end side of the distal end frame and a proximal end side connected to a ground of an external device; and
a conductive member including an electroconductive member, one end thereof being electrically and mechanically connected to the reinforcement frame, a part thereof being electrically connected to the exterior member;
wherein the conductive member is configured to elastically deform and is urged in a direction to separate the conductive member from the imaging unit.

* * * * *